United States Patent [19]
Kelley

[11] Patent Number: 6,013,061
[45] Date of Patent: Jan. 11, 2000

[54] AUTOMATIC AIR ELIMINATOR

[75] Inventor: Richard Kelley, Tyngsboro, Mass.

[73] Assignee: Microwave Medical Systems, Inc., Acton, Mass.

[21] Appl. No.: 08/950,728

[22] Filed: Oct. 15, 1997

[51] Int. Cl.[7] ................................................ A61M 5/00
[52] U.S. Cl. ............................................ 604/252; 604/126
[58] Field of Search ................................. 604/122, 126, 604/251, 252

[56] References Cited

U.S. PATENT DOCUMENTS

| 3,677,248 | 7/1972 | McPhee . | |
|---|---|---|---|
| 4,227,525 | 10/1980 | Lundquist . | |
| 4,568,366 | 2/1986 | Frederick et al. | 55/159 |
| 4,572,724 | 2/1986 | Rosenberg et al. . | |
| 4,643,713 | 2/1987 | Viitala . | |
| 4,662,906 | 5/1987 | Matkovich et al. | 55/159 |
| 4,900,308 | 2/1990 | Verkaart | 604/126 |
| 5,074,844 | 12/1991 | Zdeb et al. | 604/83 |
| 5,484,474 | 1/1996 | Weinstein et al. | 96/209 |
| 5,674,200 | 10/1997 | Ruschke et al. | 604/126 |
| 5,779,674 | 7/1998 | Ford | 604/126 |

FOREIGN PATENT DOCUMENTS

| 0 318 993 | 6/1989 | European Pat. Off. . |
|---|---|---|
| 0 478 914 A1 | 4/1992 | European Pat. Off. . |
| 0 676 213 A2 | 10/1995 | European Pat. Off. . |
| 195 06 506 | 8/1996 | Germany . |

OTHER PUBLICATIONS

Patient Safety, Epidemiology, And Education 1, Anesthesiology, V77, No. 3A, Sep. 1992, Performance of Level 1 Air Eliminator at High and Low Flow Rates, M.W.B. Hartmannsgruber, M.D. et al.

*Primary Examiner*—Wynn Wood Coggins
*Assistant Examiner*—LoAn H. Thanh
*Attorney, Agent, or Firm*—Cesari and McKenna, LLP

[57] ABSTRACT

An automatic air eliminator includes an elongated housing defining an interior chamber having a top wall, a bottom wall and a substantially cylindrical side wall centered on an axis. A vent opening is present in the chamber top wall and a hydrophobic membrane covers the vent opening. The housing has a fluid outlet passage centered on the axis in the bottom wall of the chamber and a fluid inlet passage in the chamber side wall at a location adjacent to the top wall. That inlet passage is curved about the axis so that fluid inflow to the passage enters the chamber tangentially and circulates about the axis to the fluid outlet to minimize fluid turbulence and to maximize the residence time of the fluid housing.

13 Claims, 2 Drawing Sheets

AUTOMATIC AIR ELIMINATOR

This invention relates to an air eliminator for eliminating air and other gases from a physiological fluid prior to introducing the fluid into a patient.

BACKGROUND OF THE INVENTION

An air eliminator is a medical device which is placed in the fluid line between a source of physiological fluid such as blood or I.V. fluid and a patient receiving the fluid. Gases which manifest themselves as micro-bubbles may be introduced into the fluid during administration, e.g., when changing administration sets or may appear due to a change in the temperature and/or pressure of the fluid being administered. For example, sometimes blood is delivered to a patient using pressure infusors; in that event blood is driven into the drip chambers of the I.V. set causing air bubbles which could find their way into the patient and cause an embolism. An air eliminator or air trap is intended to avoid that problem.

Conventional air eliminators usually include an elongated chamber having upper and lower ends. Physiological fluid from an elevated administration set is introduced into the upper end of the chamber and flows under gravity to the lower end of the chamber and thence to the patient. As the liquid flows through the chamber, any air or other gas entrained in the liquid tends to separate from the liquid and form bubbles which rise to the top of the chamber. A vent is provided at the top of the chamber which allows gas but not liquid to leave the chamber. Examples of such known gas eliminators are disclosed in U.S. Pat. Nos. 3,677,248 and 4,900,308.

While such known devices operate satisfactorily in many respects, they do have certain drawbacks. For example, the device in the former patent is supposed to eliminate air from an irrigation liquid used to clear away tissue from instruments being used by a surgeon. Apparently, that air may reduce the flushing efficiency. Thus, the liquid flowing through that air eliminator is not really being infused into the patient's circulatory system. As such, that device is not intended to trap all of the air in the liquid being administered. Accordingly, the liquid is introduced vertically into the top of the chamber and the flow is intended to drive air bubbles downward away from the vent opening at the top of the chamber. Resultantly, air bubbles are carried along in the fluid outflow from the chamber. Moreover, that device does not include a filter so that it would be inappropriate for use when administering a physiological fluid such as blood to a patient.

In the air eliminator described in the latter above patent, the physiological fluid is introduced laterally or diametrically into the top of the chamber. As a result, the incoming liquid carries to and impacts the opposite wall of the chamber and rolls upward as well as downward in the chamber causing turbulence and air bubbles in the downward flow. In the case of blood, the turbulence may also damage the blood cells.

In addition, that latter air eliminator is not particularly efficient in removing air from physiological fluids, particularly when the fluid is being administered at a relatively high pressure, e.g., above 300 mm Hg. See e.g., the article entitled *Performance of Level 1 Air Eliminator at High and Low Flow Rates*, by M. W. B. Hartmannsgruber, and N. Gravenstein, Annesthesiology Vol. 77, No. 3A, September 1992. It appears that because of the relatively small diameter of the chamber and the high fluid flow rate, air bubbles are pulled downward away from the vent opening at the top of the chamber. This problem is exacerbated due to the presence of a filter near the bottom of the chamber which further reduces the chamber flow crossection to an annular path only 0.1 in. wide thereby increasing the velocity of fluid even more. This produces a sucking effect which draws the air bubbles into the fluid outflow from the chamber.

Additionally, the air eliminator in the latter patent has to be oriented vertically in order to operate properly. Therefore, a separate bracket must be provided to secure the air eliminator to a support to maintain the device in a vertical orientation. This adds to the cost of the device and makes it more difficult to place the device near the patient.

SUMMARY OF THE INVENTION

Accordingly, it is an object of the present invention to provide an improved air eliminator for use in the administration of physiological fluids.

Another object of the invention is to provide an air eliminator of this type which is especially effective in removing air and other gases from blood and I.V. fluids being administered to a patient especially at high fluid flow rates.

Another object of the invention is to provide an air eliminator which can be supported solely by the I.V. line leading to the air eliminator.

Another object of the invention is to provide such an air eliminator which minimizes turbulence within the device and hence damage to a fragile fluid such as blood.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, the air eliminator herein comprises an elongated container defining an internal chamber having a relatively large cross-section. A header is mounted coaxially to the upper end of the container. The header defines a vent passage at the upper end of the chamber whose interior end contains a hydrophobic membrane which allows gas but not liquid to enter the vent passage from the chamber. Preferably also, a check valve is located at the opposite or outer end of the vent passage to allow air and other gases to leave the vent passage but not enter the passage from the outside.

In accordance with the invention, fluid is introduced into the upper end of the chamber tangentially through the side of the air eliminator. More particularly, the header includes a fluid inlet which is curved about the longitudinal axis of the air eliminator so that the fluid flowing through the inlet enters the chamber tangentially imparting a swirl to the fluid as it travels downward in the chamber. Thus, rather than impacting the chamber wall, the fluid circulates more or less parallel to the wall following a spiral-like path down the entire length of the chamber. Thus, fluid turbulence is minimized. Also, the spirally circulating liquid in the chamber has a reduced vertical velocity component. This allows more time for air and other gases to separate from the fluid, float as bubbles to the top of the chamber and pass through the hydrophobic membrane at the vent opening thereat. Moreover, because the liquid flow through the chamber has a smaller vertical component and the chamber has a relatively large cross-sectional area, the incoming fluid has less tendency to draw air bubbles in the fluid downward away from the vent passage and into the fluid outflow from the chamber.

When administering a fluid such as blood, the air eliminator should also include a relatively tall filter inside the container so that the fluid flowing through the chamber is forced to flow around and through the filter on its way to the chamber outlet at the lower end of the housing.

Due to its large diameter and tangential fluid inflow, the air eliminator herein does not have to be oriented vertically when in use. In fact, it may be tilted in any direction by as much as 45° from the vertical. Consequently, the device can be supported solely by the I.V. line leading to the header. This greatly facilitates placing the device at the proper location between the fluid source and the patient.

Yet with all of the above advantages, this fluid eliminator is composed of only a few relatively inexpensive molded plastic parts which are easy to make and to assemble. Therefore, it should find widespread use in hospitals and clinics whenever it is necessary to administer the physiological fluids to patients.

BRIEF DESCRIPTION OF THE DRAWINGS

For a fuller understanding of the nature and objects of the invention, reference should be had to the following detailed description taken in connection with the accompanying drawings, in which.

DETAILED DESCRIPTION OF AN ILLUSTRATIVE EMBODIMENT

Figure 1:
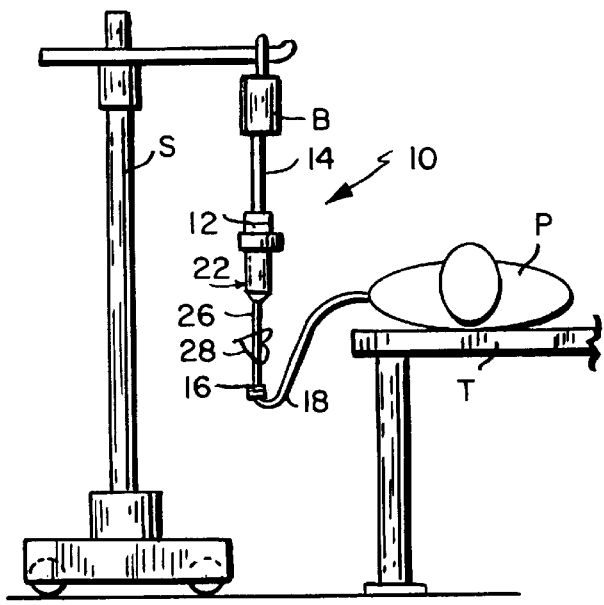
FIG. 1 depicts a fluid being administered to a patient using an air eliminator according to the invention.

In FIG. 1 of the drawings, an automatic air eliminator incorporating the invention and shown generally at 10 is connected in the fluid line between a source of physiological fluid represented by a bag B and a patient P lying on a table T. The bag B is suspended from a support S so that the bag is located well above patient P.

The air eliminator 10 has an inlet connector 12, e.g., a female Luer, releasably connected to an I.V. line 14 leading from bag B and a fluid outlet connector 16, e.g., a male Luer, releasably connected to an I.V. line 18 leading to an infusion site in the patient P.

Figure 4:
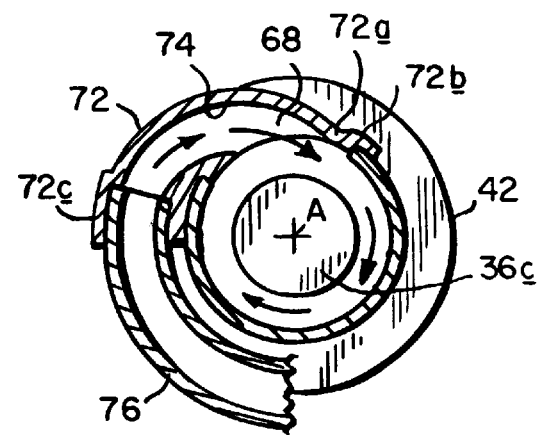
FIG. 4 is a sectional view taken along line 4—4 of FIG. 3.

The air eliminator includes a generally cylindrical housing 22 having a longitudinal axis A (FIG. 4). Fluid, e.g., blood, from bag B flows into the upper end of the housing via inlet connector 12 and exits the housing via an outlet tube 26 leading from the lower end of the housing to the outlet connector 16. Since the bag B is elevated above patient P, there is a pressure head which causes the blood in bag B to flow through the air eliminator 10 to the patient at a flow rate dependent upon the height of the bag above the patient. Thus, by varying the height of the bag, flow rates such as 350 cc/min., can be achieved. Also, by forcibly collapsing bag B using a conventional pressure infuser (300 mmHg), even higher fluid flow rates of over 1000 cc/min. may be achieved.

Preferably, the air eliminator 10 includes a conventional binary clamp 28 on the outlet tube 26 to stop fluid flow from housing 22 when it becomes necessary to disconnect the air eliminator from patient P.

Figure 2:
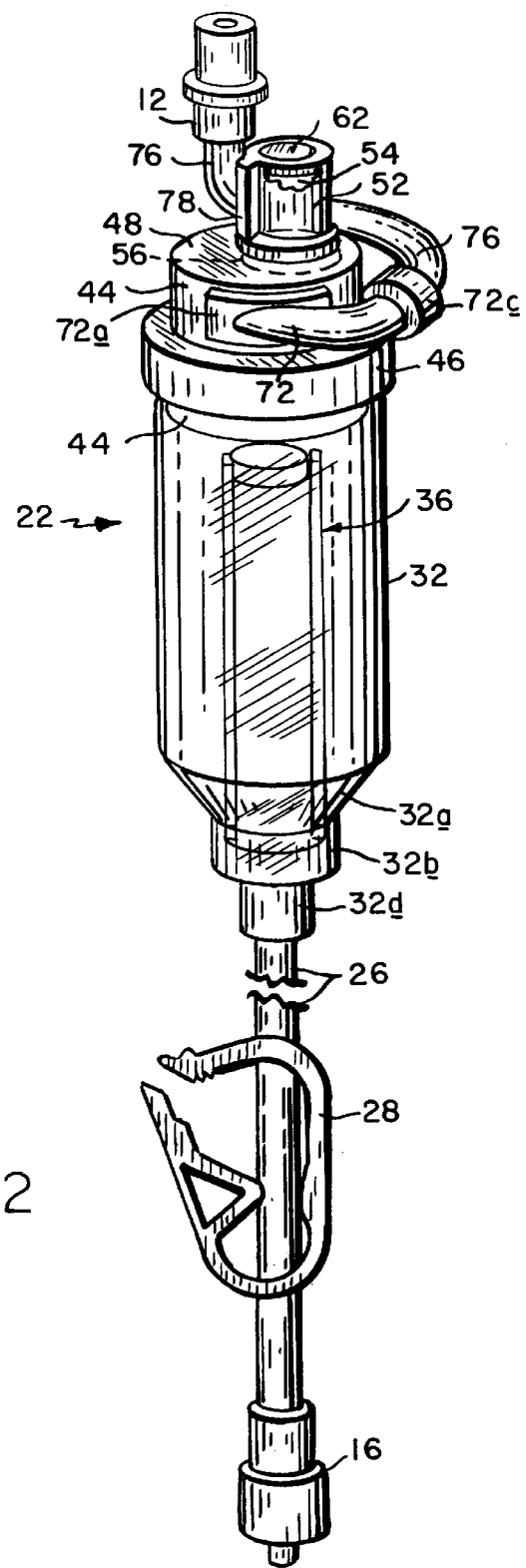
FIG. 2 is a perspective view, with parts broken away, on a much larger scale showing the air eliminator in greater detail.
Figure 3:
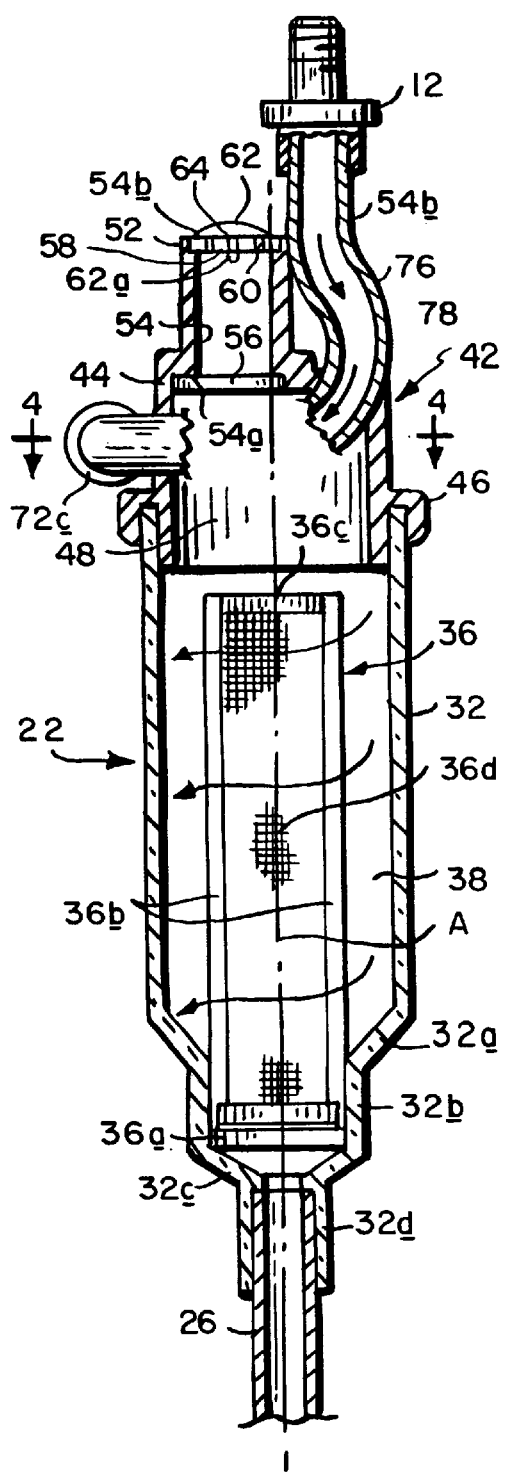
FIG. 3 is a vertical sectional view of the FIG. 2 air eliminator.

FIGS. 2 and 3 show the housing 22 in greater detail. It comprises an elongated generally cylindrical, transparent plastic tubular container 32 open at the top. The container has an internal diameter of about 1.0 inch. and is about 3.5 inches long. The container lower end necks down at 32a to a waist 32b. An additional narrowing at 32c leads to a cylindrical outlet 32d centered on axis A. The upper end segment of tube 26 is secured within outlet 32d by a solvent bond or the like.

Extending up from the bottom of container 32 concentric to axis A is an elongated tubular filter shown generally at 36. Filter 36 includes a ring 36a which is seated snugly at the bottom of container waist 32b. A pair of legs 36b extend up from ring 36a at diametrically opposite sides thereof, the upper ends of the legs being connected by a disc 36c. Supported between elements 36a–36c is a sheet 36d of filter material e.g., 200 micron mesh, formed as a tube whose axis A lies on the axis of the air eliminator as a whole and whose interior leads to outlet 32d. As best seen in FIG. 3, the filter 36 extends almost to the top of container 32 and has a diameter of about 0.5 in. so as to define with the container wall a relatively wide annular interior fluid flow space 38 whose cross-sectional area is at least as large as that of the filter.

Housing 22 also includes a header shown generally at 42 which is mounted to the top of the container. The header includes a cylindrical cap 44 centered on axis A whose outer diameter is comparable to the inside diameter of container 32 so that the cap can plug into the top of the container. Cap 44 is provided with a peripheral flange or lip 46 which engages over the upper edge of container 32 so as to secure the cap to the container. Preferably, the header is permanently sealed to the container at flange 46 by solvent bonding or the like. When installed on the container, the header 42 defines an unobstructed chamber 48 between the top of the cap 44 and the annular flow space 38.

Still referring to FIGS. 2 and 3, a cylindrical stack 52 extends up from the top of cap 44. The stack is offset from axis A and defines an interior passage 54 which leads from that chamber to the atmosphere. The lower end of passage 54 is counterbored at 54a to provide a seat for a discoid hydrophobic membrane 56 which may be secured in place by solvent bonding or the like. Also, the upper end of passage 54 is counterbored at 54b to accommodate a disc 58 containing a plurality of through-holes 60. Positioned on top of disc 58 is a mushroom-shaped diaphragm 62 having a stem 62a secured in a central opening 64 in disc 58. Diaphragm 62 functions as a one-way valve to allow gas to flow from vent passage 54 through the holes 60 to the outside, but to prevent gas flow in the opposite direction. Thus, the valve prevents air from entering the air eliminator 10 through passage 54 in the event the device is positioned below patient P.

As best seen in FIG. 4 an arcuate opening 68 is provided in the side wall of the cap 44. The fluid conducted to the air eliminator is introduced into the chamber 48 through this opening. More particularly, the header 42 includes a tubular manifold 72 defining a curved inlet passage 74. The discharge or exit end 72a of the manifold is provided with an arcuate pad 72b which is bonded to the side of the cap 44 so that the manifold passage 74 opens into the chamber 48 more or less tangentially. The manifold 72 extends around cap 44 an arcuate distance of about 90° so that the manifold entrance end 72c is positioned at the point of closest approach to the offset header stack 52. A length of tubing 76 extends from the entrance end 72c of manifold 72 to the air eliminator's inlet connector 12. Preferably, the tubing 76 is formed as a coil so that the tubing follows a generally curved path from the manifold to connector 12. Preferably also, a semicylindrical seat 78 is provided at the side of stack 52 near the center of header 42 to which the upper end segment of tubing 76 may be secured, e.g., by solvent bonding or an adhesive, so that the connector 12 is maintained near and parallel to axis A.

All of the components of the air eliminator 10 are made of medical grade plastic materials which can withstand ethylene oxide (ETO) and gamma sterilization.

When the air eliminator 10 is in use as shown in FIG. 1, the fluid, e.g., blood, flows under gravity from bag B into the housing 22. As shown in FIGS. 3 and 4, the blood enters the housing through the coiled tubing 76 and manifold 72. The blood issuing from manifold 72 enters the chamber 48 at the top of the housing tangentially as shown by the arrows in FIGS. 3 and 4 so that the blood circulates around the chamber 48 and may follow an unobstructed helical path all the way down to the bottom of the annular space 38. Therefore, the vertical component of the fluid flow velocity is minimized along the entire length of the housing. That fact, coupled with the fact that the chambers 38 and 48 have unusually large diameters or cross sections maximizes the residence time of the fluid in the housing 22. During this time, substantially all air and other gases entrained in the blood separate from the blood and rise as micro-bubbles to the top of the chamber 48 where they collect at the hydrophobic membrane 56. The membrane allows those gases to pass into the vent passage 54 whence they are vented to the atmosphere. On the other hand, the membrane 56 blocks egress of blood from the housing 22 and header 42. Resultantly, the blood leaving unit 10 is devoid of air and other gases even when the unit is used during a pressure infusion.

The fact that the blood follows a helical path along the header 42 and housing 22 also minimizes turbulence and fluid impacts with the housing wall thereby assuring that there will be minimum damage to blood cells.

After the administration of fluid has been completed, clamp 28 may be placed in its clamping position thereby stopping fluid flow through the air eliminator. Then, the connectors 12 and 16 may be uncoupled from I.V. lines 14 and 18, respectively. Preferably, the connectors 12 and 16 are then coupled together to form a closed loop to prevent spillage of any fluid remaining in the air eliminator and allowing the unit to be disposed of in an approved manner.

It is an important feature of the invention that the extra large diameter of housing 22 coupled with the tangential fluid inflow allows the air eliminator 10 to operate properly even though it is displaced from the vertical by as much as 45°. In other words, the unit tilted thusly still allows sufficient time for substantially all the entrained gases to become separated from the blood and form micro-bubbles which float to the top of chamber 48 for venting through the hydrophobic membrane 56. Therefore, it is not necessary to provide a special bracket or fixture to maintain the air eliminator in a vertical orientation. Rather, the unit can simply hang from the I.V. line 14 to which it is connected as shown in FIG. 1.

As seen from the drawing figures, air eliminator 10 is composed of a relatively few molded plastic parts. These parts are easy to manufacture in quantity and are easy to assemble. Therefore, the overall cost of the unit can be kept to a minimum allowing its use as a disposable item in hospitals and clinics where physiological fluids are routinely administered to patients.

It will thus be seen that the objects set forth above, among those made apparent from the preceding description, are efficiently attained and, since certain changes may be made in the above description without departing from the scope of the invention, it is intended that all matter contained in the above description or shown in the accompanying drawings shall be interpreted as illustrative and not in a limiting sense.

It should also be understood that the following claims are intended to cover all of the generic and specific features of the invention described herein.

What is claimed is:

1. An automatic air eliminator comprising an elongated housing (22) defining an interior chamber having a top wall, a bottom wall and a substantially cylindrical side wall centered on an axis A;

a vent passage (54, 60) in the chamber top wall;

a hydrophobic membrane (56) spanning said vent passage (54, 60);

a fluid outlet passage (32d) in the bottom wall of said chamber;

a fluid inlet opening (68) in the chamber side wall at a location adjacent to said top wall, said inlet opening being positioned relative to said axis so that fluid inflow to said inlet opening enters the chamber tangentially and circulates about said axis to said bottom wall and flows to the fluid outlet passage (32d), and a curved inlet tube having a first end connected to said inlet opening and a second end arcuately spaced about said axis from said inlet tube first end; an inlet connector connected to said inlet tube second end, and securing means for securing the inlet tube to said housing so that the inlet connector lies substantially parallel to said axis.

2. The air eliminator defined in claim 1 wherein said vent passage is offset from said axis, and said securing means lie close to said axis.

3. The air eliminator defined in claim 1 and further including an inlet tube coupled to the inlet connector for suspending the air eliminator and conducting fluid thereto.

4. The air eliminator defined in claim 1 and further including an outlet tube which is appreciably longer than said housing and has a first end connected to said outlet passage and a second end, and an outlet connector connected to the outlet tube second end, said outlet connector being adapted to be coupled to said inlet connector.

5. The air eliminator defined in claim 4 wherein said inlet and outlet connectors are, respectively, female and male Luer connectors.

6. The air eliminator defined in claim 1 wherein said outlet passage is centered on said axis, and further including a tubular filter extending up from the chamber bottom wall on said axis, the interior of the filter being in fluid communication with said outlet opening the top of the filter being located below said inlet passage, the crossectional area of the filter being substantially less than that of the chamber so that a relatively large annular interior space exists between the filter and the chamber side wall.

7. The air eliminator defined in claim 6 wherein said filter extends up from the chamber bottom wall almost to said fluid inlet opening.

8. An automatic air eliminator comprising an elongated container having a top, a bottom wall and a cylindrical side wall extending up from the bottom wall and being centered on an axis;

a fluid outlet in the bottom wall on said axis;

a tubular filter extending up from the container bottom wall on said axis and having an interior, said interior being in fluid communication with said outlet and said filter defining with said side wall an annular space in said container;

a cap closing the top of the container, said cap having a top wall and a cylindrical side wall centered on said axis and defining a chamber above said filter;

a vent passage in the cap top wall;

a hydrophobic membrane spanning said vent passage, and means defining an arcuate fluid inlet opening in the cap side wall, said opening following an imaginary curved line about said axis and being elongated circumferentially whereby fluid inflow to said opening enters said chamber tangentially and circulates along an unobstructed helical path into said annular space and flows through said filter to said fluid outlet.

9. The air eliminator defined in claim 8 and further including a curved opening tube having a first end connected to said inlet and a second end connected to said cap at a location thereon spaced arcuately about said axis from said first end;

an inlet connector connected to said inlet tube second end, and securing means for securing the inlet tube to the header so that the inlet connector lies substantially parallel to said axis.

10. The air eliminator defined in claim 9 wherein said vent passage is offset from said axis and said securing means lies close to said axis.

11. The air eliminator defined in claim 9 and further including an inlet tube connected to the inlet connector for suspending the air eliminator and conducting fluid thereto.

12. The air eliminator defined in claim 8 wherein said annular space has a cross sectional area that is substantially larger than that of said filter.

13. The air eliminator defined in claim 12 wherein said filter extends up from the container bottom wall almost to the top of the container.

* * * * *